United States Patent
Filkins et al.

(10) Patent No.: US 8,063,385 B2
(45) Date of Patent: Nov. 22, 2011

(54) METHOD AND APPARATUS FOR ULTRAVIOLET SCAN PLANNING

(75) Inventors: Robert John Filkins, Niskayuna, NY (US); Robert William Tait, Niskayuna, NY (US); Kevin Bernard Kenny, Niskayuna, NY (US); Christina Chirappuram Royce, Niskayuna, NY (US)

(73) Assignee: General Electric Company, Niskayuna, NY (US)

(*) Notice: Subject to any disclaimer, the term of this patent is extended or adjusted under 35 U.S.C. 154(b) by 349 days.

(21) Appl. No.: 12/474,306

(22) Filed: May 29, 2009

(65) Prior Publication Data
US 2010/0301230 A1 Dec. 2, 2010

(51) Int. Cl.
*G01N 21/64* (2006.01)
(52) U.S. Cl. .................. 250/458.1; 250/459.1
(58) Field of Classification Search ........... 250/458.1, 250/459.1
See application file for complete search history.

(56) References Cited

U.S. PATENT DOCUMENTS

| | | |
|---|---|---|
| 6,405,074 B1 | 6/2002 | Banerjee |
| 6,553,135 B1 | 4/2003 | Douglass et al. |
| 6,763,262 B2 | 7/2004 | Hohla et al. |
| 6,775,402 B2 | 8/2004 | Bacus et al. |
| 6,992,760 B2 * | 1/2006 | Mohun et al. ............. 356/317 |
| 7,235,045 B2 | 6/2007 | Wang et al. |
| 7,248,403 B2 | 7/2007 | Nakagawa |
| 2003/0147552 A1 | 8/2003 | Foran et al. |

FOREIGN PATENT DOCUMENTS

| | | |
|---|---|---|
| WO | WO0248692 A1 | 6/2002 |
| WO | WO2005036451 A1 | 4/2005 |
| WO | WO2006134444 A1 | 12/2006 |
| WO | WO2007138369 A1 | 12/2007 |
| WO | WO2009006696 A1 | 1/2009 |

OTHER PUBLICATIONS

PCT International Search Report dated Sep. 24, 2010 and Written Opinion.
Borovansky, "Autofluorescence of Melanins Induced by Ultraviolet Radiation and Near Ultraviolet Light. A Histochemical and Biochemical Study", The Histochemical Journal 2001, 33(5): 273-81.

* cited by examiner

*Primary Examiner* — Mark R Gaworecki
(74) *Attorney, Agent, or Firm* — Eileen W. Gallagher

(57) ABSTRACT

The invention provides method for locating one or more substantially circular-shaped tissue sample positioned on a solid support. The method involves the steps of transmitting light of a preselected wavelength onto a tissue sample, wherein the light induces the tissue sample to autofluoresce, identifying the center location of the tissue sample using the autofluoresced light, correlating the coordinates of the center location of the tissue sample on the solid support using an x, y-coordinate system, and mapping the coordinates of the tissue sample on the solid support to differentiate tissue sample containing regions from blank regions on the solid support. In a second aspect, the invention provides an apparatus for locating one or more substantially circular-shaped tissue sample positioned on a solid support.

21 Claims, 2 Drawing Sheets

METHOD AND APPARATUS FOR ULTRAVIOLET SCAN PLANNING

BACKGROUND

In medical imaging of prepared tissue samples for microscopic analysis, there is the need to first locate the tissue on a solid support. In order to image the tissue sections most efficiently, the system must first know exactly where tissue is located on the solid support. In the simplest description, the system must look at the entire solid support and identify which sections are tissues, which are glass, label and debris. The tissue location is then converted to a region envelope. The coordinates of the region are then mapped in the position space of the microscope stage. This allows the microscope motion to be programmed to cover the appropriate areas of the solid support, and avoid areas of waste where no tissue exists. This technique is often referred to as scan planning.

While it may be preferred to extract information directly about the location of tissue during analysis, the use of standard fiducials is problematic due to slide-to-slide and operator-to-operator variability. Tissue-based scan planning is often preferred as it allows more repeatable and reliable plans while avoiding requirements for special slides or particular mounting techniques.

Typical approaches for scan planning involve performing a coarse scan of the complete solid support at a relatively low magnification (e.g. 1.25×) in order to localize the tissue which is digitized and reconstructed to provide a user with a magnified image of the specimen prior to a more detailed analysis.

Current methods often rely on color or texture to differentiate tissue from the solid support. There are several potential problems with these methods because they are likely to catch ink or stray marks on the slide, as well as the fiducial crosshatching on the edges of some slides. In the case of tissue labeled with fluorescent dyes, the image acquisition time is often slow; there is the possibility that a stained tissue sample may undergo photo bleaching before the imaging process is complete. Further, when a tissue is stained with fluorescent dyes, often the dye necessarily localizes to a specific sub-region of the tissue and does not completely cover the tissue, making it difficult to accurately discern tissue from non-tissue as is possible when using other dyes such as hematoxylin and eosin (H&E) which are visible in brightfield imaging. Therefore fluorescent dyes necessitate other methods of detection. Finally, current methods do not typically work well for unstained tissue sections, as thin tissue sections are essentially transparent in visible light and therefore do not provide enough signal information to process accurately.

BRIEF DESCRIPTION

In a first aspect, the invention provides method for locating one or more substantially circular-shaped tissue sample positioned on a solid support. The method involves the steps of transmitting light of a preselected wavelength onto a tissue sample, wherein the light induces the tissue sample to autofluoresce, identifying the center location of the tissue sample using the autofluoresced light, correlating the coordinates of the center location of the tissue sample on the solid support using an x, y-coordinate system, and mapping the coordinates of the tissue sample on the solid support to differentiate tissue sample containing regions from blank regions on the solid support.

In a second aspect, the invention provides an apparatus for locating one or more substantially circular-shaped tissue sample positioned on a solid support. The apparatus comprises a imaging microscope having at least one objective lens to acquire images at different magnifications and a stage to hold the sample on the solid support, an excitation source to illuminate the sample on the stage, a digital image device connected to the microscope to acquire and digitized the images of the sample, a storage device in communication with the digital image device capable of storing the digitized images of the sample; and a processor in communication with the storage device and capable of categorizing the digital images and generating one or more match filters based on a correlation factor.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The following detailed description is exemplary and not intended to limit the invention of the application and uses of the invention. Furthermore, there is no intention that the invention be limited by any theory presented in the preceding background of the invention or the following detailed description of the figures.

In accordance with one embodiment, a method is described in which the location of a substantially circular-shaped tissue sample on a solid support is determined using autofluorescence. In one embodiment, the method comprises illuminating the tissue sample using a near-UV light resulting in autofluorescence. Autofluorescence refers to the energy and magnitude of photons emitted by endogenous compounds within a tissue, or tissue sample, upon being exposed to an external source of photons in the absence of administration or binding of any exogenous fluorescing compound, as distinguished from the radiation emitted following the administration and binding of such fluorescing compound and exposure to an external source of photons. The photon energy is typically in the UV or visible range.

A macro-image of the tissue sample undergoing autofluorescence is obtained using a standard photographic lens in order to capture the entire solid support, including any identification marking, in a single image. Identification markings generally refer to indicators on the solid support such as crosshatch markings positioned at the edges or corners of the solid support.

The solid support may include, but is not be limited to, a microscope slide, a tissue micro-array slide, or a microtiter plate. The sample is illuminated prior to any fluorescent labeling. Once a tissue image is obtained, it is processed to identify the location of the tissue sample on the solid support.

Figure 1:
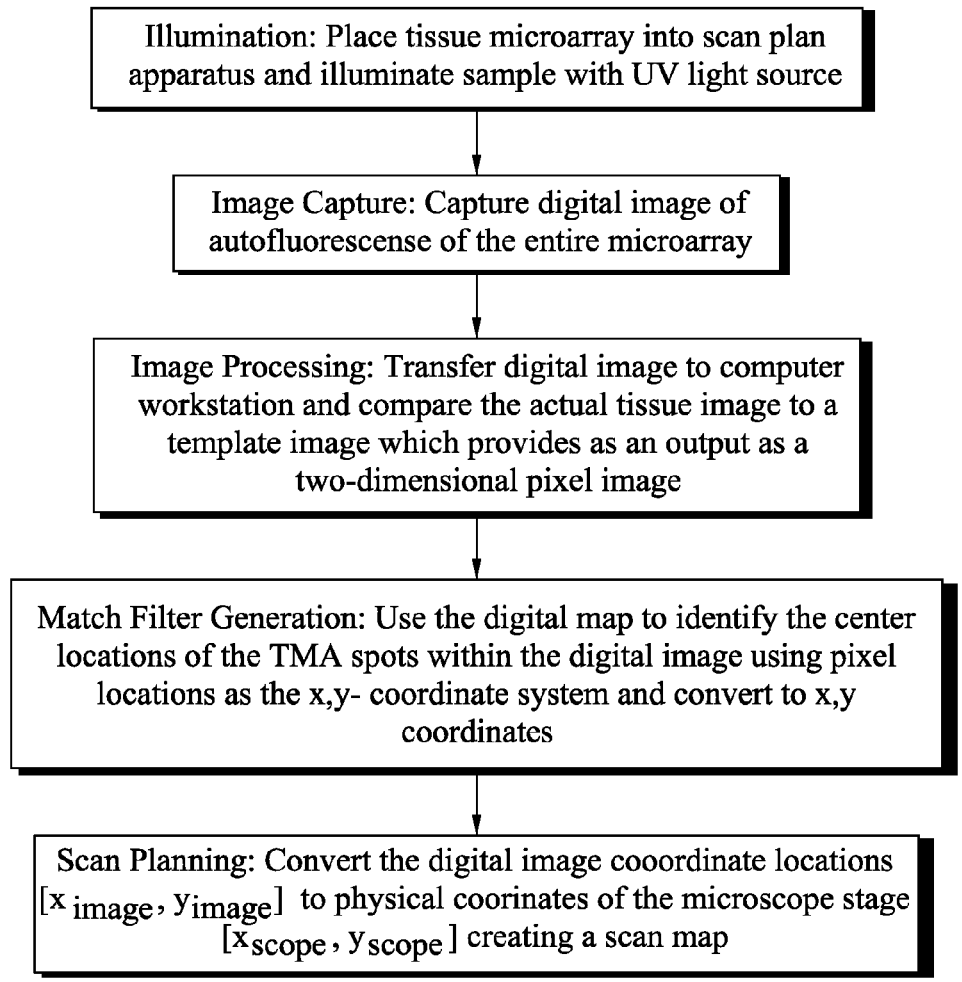
FIG. 1 is a schematic diagram of a multi-step method of image acquisition and analysis embodying the invention.

FIG. 1 illustrates an exemplary technique that may be employed to acquire images for use in certain embodiments of the invention. FIG. 1 shows a schematic diagram of a multi-step method of image acquisition and analysis comprising transmitting light of a preselected wavelength onto a tissue sample on a solid support wherein the light induces the tissue sample to autofluoresce, identifying the center location of the tissue sample using the autofluoresced light, correlating the center locations with a preexisting template of the tissue sample to create a second digital image that assigns pixel values to each area of the digital image, creating a two-dimensional coordinate system and, using the pixel values, mapping the coordinates of the tissue sample on the solid support to differentiate tissue sample containing regions from blank regions on the solid support.

In a first step, the method comprises illuminating a substantially circular-shaped tissue sample on a solid support using a near UV light resulting in autofluorescence. In one embodiment, a standard mercury halide lamp may be used as a light source. Substantially circular-shaped refers to a tissue sample wherein the distance from points along the outer boundary of the tissue sample to a centroid point within the sample are of a similar length resulting in a pattern that is recognized as circular. The centroid point corresponds to the center location of the tissue sample. Such circular patterns are described in Proc. Natl. Acad. Sci. USA Vol. 95, pp. 12783-12786, October 1998.

The substantially circular-shaped tissue sample may include any tissue material such as a tissue sample contained on a tissue micro-array (TMA), a biopsy tissue sample, or a biological sample. The tissue sample may be frozen or fixed with tissue preservative such as formalin, or otherwise treated. The tissue sample may be unstained or stained in order to improve contrast in visible light. In some embodiments the tissue sample may be a whole cell, a cell constituent, a cytospin, or a cell smear. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

In some embodiments, a tissue sample includes tissue sections from healthy or diseased tissues (e.g., tissue sections from colon, breast tissue, prostate). A tissue sample may include a single part or piece of a tissue section, for example, a thin slice of tissue or cells cut from a tissue section. In some embodiments, the same section of tissue sample may be analyzed at both morphological and molecular.

The tissue sample may be permanently or temporarily adhered to a solid support in order to allow for its analysis, transfer and movement during the preparation and imaging processes. Solid supports may include a slide, a microtiter plate, disk, Petri dish, gel plate, or block cassette. The solid support may be made of glass, plastic or other material.

The tissue sample may also be part of a tissue micro-array (TMA). As such the tissue sample is one of multiple samples contained within test wells arranged on a single micro-array slide. The number of test wells, and therefore the number of individual tissue samples on the single slide, is variable depending on the array design. For example, a TMA may be designed such that each individual tissue sample comprises a circular test well that is 0.6 mm in diameter at a spacing of 0.7-0.8 mm resulting in a surface area of each tissue sample of 0.282 $mm^2$.

In a second step, the autofluoresced light is used to capture a digital image of the sample. In some embodiments, it may be desirable to capture the complete image of the tissue sample on the solid support in a single image using a standard photographic lens under low magnification. In some alternative embodiments, only a portion of the solid support may be captured. A single image may also include identification markings on the solid support such as an adhesive label or a crosshatch marking.

The sample may be illuminated before any fluorescent labeling of the sample occurs. Non-fluorescent dyes and indicators such as DAPI may be applied to the sample, prior to the image capture process, provided the dyes do not interfere with autofluorescene of the sample. The image capture process may comprise using a camera, which includes a processor and a lens. The processor is configured to receive the light from the lens resulting in a digital image In a third step, the digital image of the tissue sample from the camera is processed in order to compare the digital image to a template image containing a simplified representation of the size and shape of the tissue sample. Where the tissue sample is part of a tissue micro-array, the template image is representative of the number and location of each individual tissue sample arranged in test wells.

In one embodiment, the digital image and template image are compared. The process of comparing the actual tissue image to a template image provides as an output a two-dimensional pixel image, which is scaled and recorded, and includes the center location of the tissue sample. The comparative process may involve using a zero-mean cross-correlation, a normalized power spectral density (PSD) cross-correlation, or a combination thereof, between the digital image and the template image in the spatial domain.

If the tissue sample is a TMA comprised of test wells, the resulting two-dimensional comparative pixel image may yield a bright spot located at the center of each TMA test well. The bright spot center locations may be converted into a two dimensional grid in the coordinate space defined by the microscope slide. The two dimensional grid may be a Cartesian coordinate system with two axes, at right angles to each other, defining a plane (an xy-plane).

As shown further in FIG. 1, in one embodiment the comparative process generates in a forth step, a two-tone match filter image corresponding to the pixel size of the tissue sample on the solid support. A two-tone match filter is a two-dimensional digital construct designed to represent an idealized version (in spatial or spectral coordinates) of an object that is to be identified or extracted from another digital image. In the case where the tissue sample is part of a TMA comprised of test wells, the match filter may be used to process the TMA image creating a macro image of each tissue sample.

The two-tone match filter may be a white image on a black background wherein the size of the white image, in pixels, corresponds to the size in pixels of the tissue sample. In certain embodiments, the macro image of the tissue sample is created using a zero-mean cross-correlation wherein the spatial pixel values of the tissue sample's digital image is scored based on intensity and is converted into a spectral domain image. A suitable spectral domain transformation includes Fourier transform, wavelet transform, discrete Fourier transform, discrete cosine transform, normalized power spectral density calculation, or similar series representation.

In certain embodiments an image transfer function, such as a fast Fourier Transfer (FFT), is performed on both the match filter and the test sample image. A new image may be generated where each pixel is assigned an intensity value based on a best-fit analysis to the match filter image.

Knowing the dimensions and number of TMA test wells an operator may determine the number of image captures, or fields of view, needed to capture the TMA in its entirety and, in a fifth step as shown in FIG. 1, a scan plan may be created that gives the series of coordinates to capture from in each image capture. For example a tissue array that would require a two by two set of image captures, center point as reference when calculating the coordinates of each of the four image captures. Given that (x,y) is the center of the TMA and w is the width of one capture the output coordinates would be (x−w/2, y−w/2), (x+w/2, y−w/2), (x+w/2, y+w/2) and (x−w/2, y+w/2). The grid in the coordinate space of the TMA may be used to image the array for qualitative or quantitative analysis.

Figure 2:
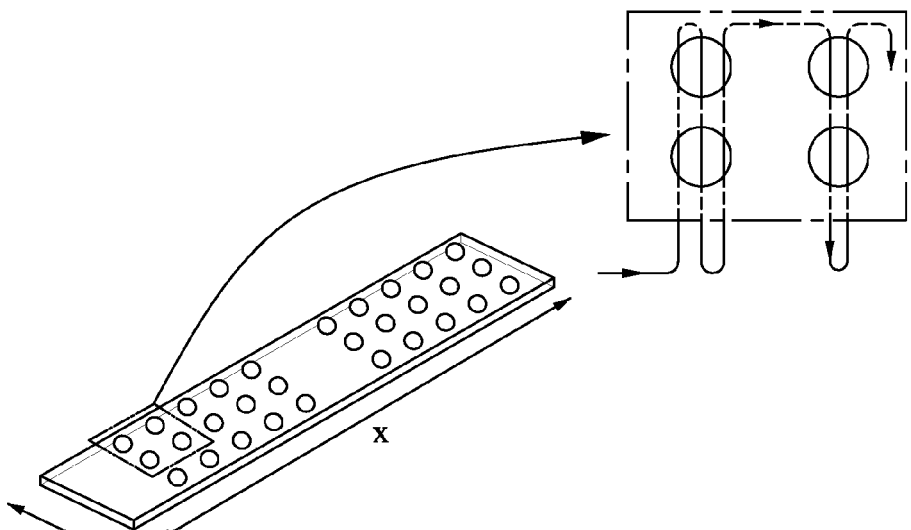
FIG. 2 is a schematic representation of a tissue microarray showing the x-y direction of image acquisition using a mask filter based on an embodiment of the invention.

FIG. 2 is a schematic representation of a tissue micro-array showing the x-y direction of image acquisition using a scan plan based on a Cartesian coordinate system, wherein x and y are two perpendicular directed lines defining an x,y plane.

In one embodiment a scan plan may be generated by first determining a threshold value to distinguish bright spots that are intense enough to be TMA test well centers from those that are not. Starting at the spot of maximum intensity, an algorithm may be used to iteratively select the area and assigns it as a center point of a single test well. The area surrounding the center point, corresponding to the predicted diameter of a test well, is blacked out. The purpose of blacking out the near region to a bright spot is to keep from choosing several 'centers' for a single spot. The area of the next highest pixel intensity is then selected and the process repeated until the entire microscope slide is analyzed for bright spots.

Based on input on the size of the image capture from the microscope and the size and number of bright spots, the algorithm outputs coordinates for each of the predicted TMA test wells. These coordinates are ordered, creating a scan plan such that the movement of the stage is minimized. For example, the scan plan may start from a test well located on the bottom left of the TMA (as you look down on the slide) and snake back and forth across the test well rows working towards the top of the TMA slide. For each test well a similar serpentine pattern is used to economize motion.

As illustrated in FIG. 2, the microscope stage may be moved, based on a Cartesian coordinate system (x,y plane) to allow scan imaging of a TMA 30 starting from the test well on the bottom left 32 and moving back and forth across the rows working towards the top of the TMA 34 in a serpentine pattern 36. Image acquisition occurs based on the scan plan as represented by a solid line.

Figure 3:
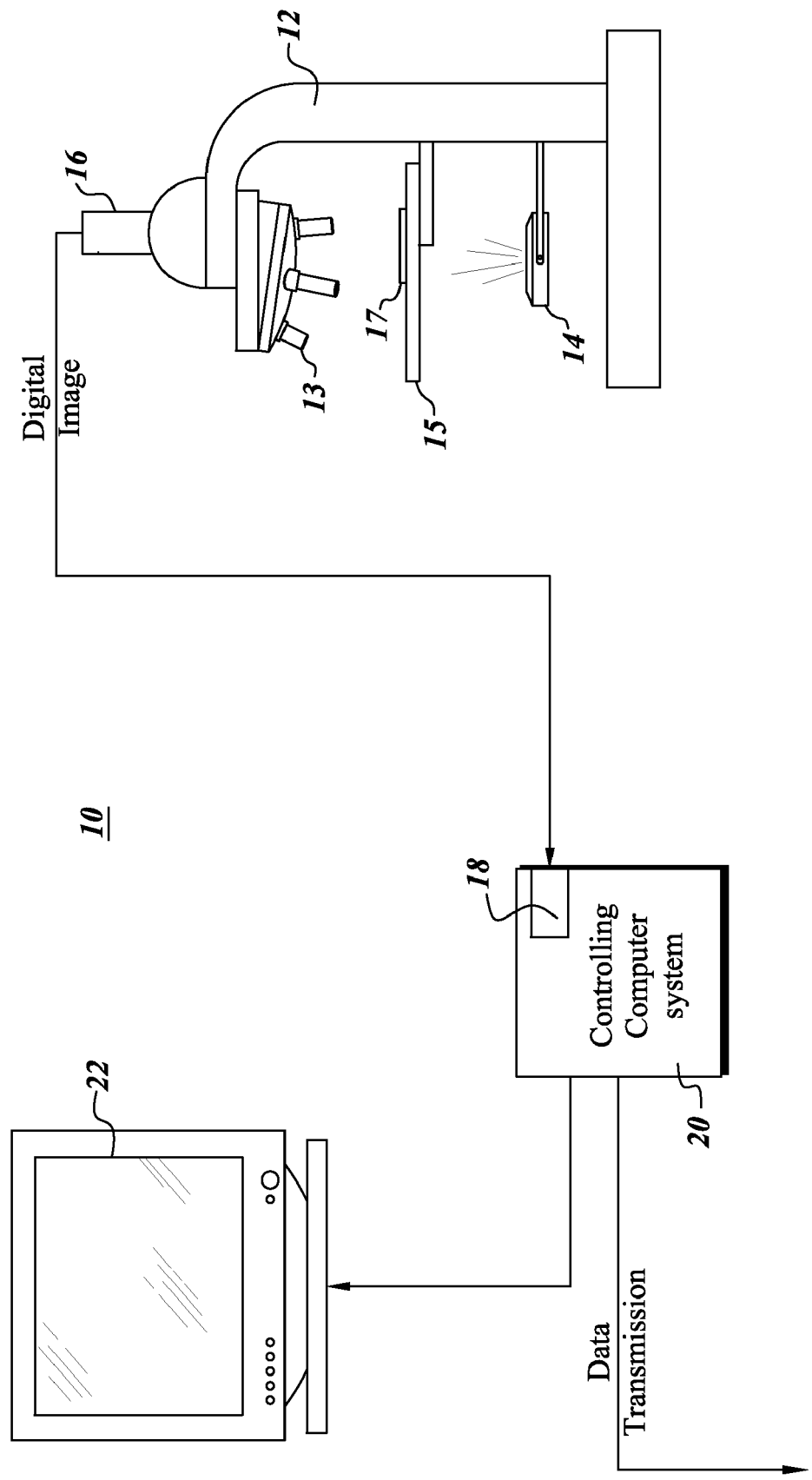
FIG. 3 is an illustration of an automated system capable of locating a tissue sample on a solid support.
Figure 1:
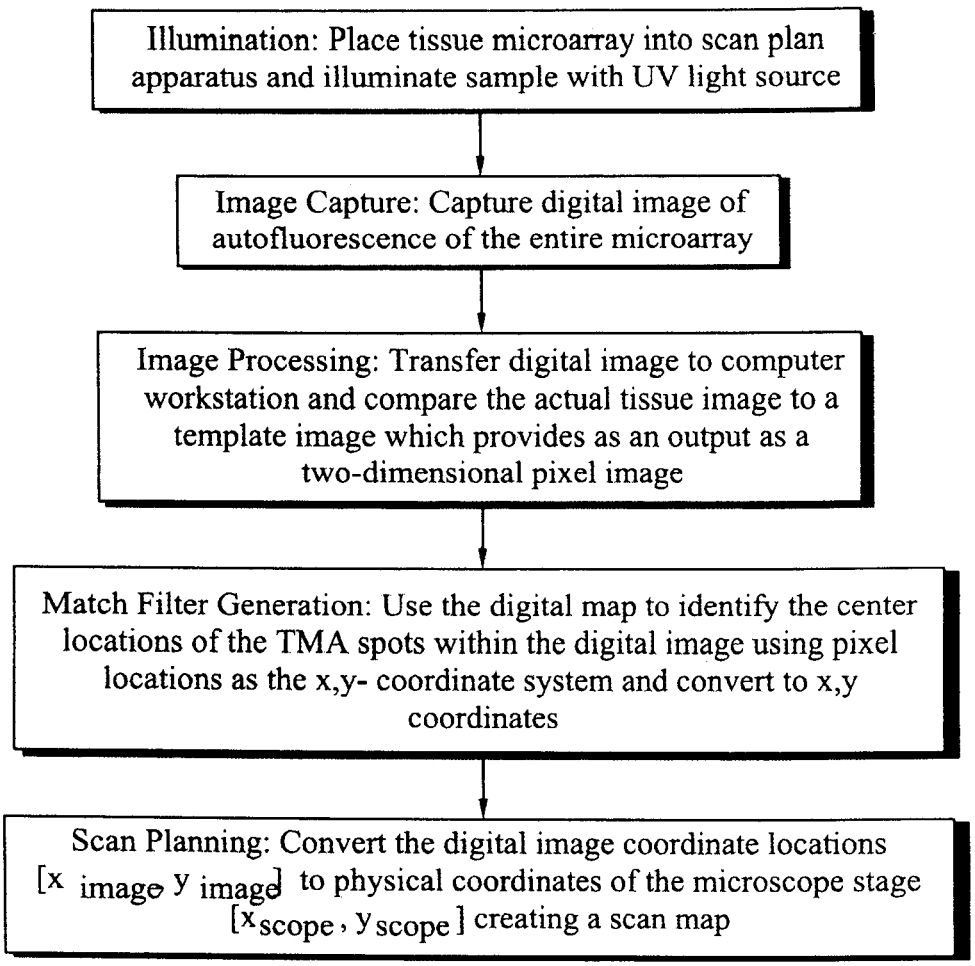

As shown in FIG. 3, an automated system 10 may be used for carrying out the methods are described herein. As illustrated, the system 10 may include an imaging microscope 12, and a excitation source 14, a digital image device 16, a storage device 18 for at least temporarily storing one or more images, and a processor 20 that categorizes the images and generates one or more match filters based on a correlation factor.

The imaging microscope 12 may have at least one objective lens 13 to acquire images at different magnifications and a stage 15 to hold a tissue sample 17 mounted on a solid support. The stage is used to position the sample to be viewed at a specific location on the solid support. The excitation source 14 comprises a light source for illuminating the tissue sample on the solid support using a near UV light resulting in autofluorescence.

The digital image device 16 may be comprised of a digital camera, not shown, to acquire images of the tissue sample during autofluorescence. The image device 16 is preferably capable of auto focusing and then maintaining and tracking the focus feature as needed throughout processing.

The storage device 18 may comprise, but is not necessarily limited to, any suitable hard drive memory associated with the processor 20 such as the ROM (read only memory), RAM (random access memory) or DRAM (dynamic random access memory) or any suitable disk drive memory device such as a DVD or CD, or a zip drive or memory card. The storage device may be remotely located from the processor 20 and yet still be accessed through any suitable connection device or communications network including but not limited to local area networks, cable networks, satellite networks, and the Internet, regardless whether hard wired or wireless. The processor 20 may be a CPU (central processing unit) and may comprise a microprocessor, microcontroller and a digital signal processor (DSP).

System 10 may further comprise a display device 22 for displaying one or more of the images and a transmitting device, not shown, for transmitting digital information. The display device 22 may comprise any suitable device capable of displaying a digital image such as, but not limited to, devices that incorporate an LCD or CRT. The transmitting device may comprise any suitable means for transmitting digital information over a communications network including but not limited to hardwired or wireless digital communications systems.

In one of the embodiments, the system may be may be incorporated as components of an analytical device such as an automated high-throughput system that is capable of staining and imaging TMAs in one system and still further analyzes the images. As such, in one embodiment, the system is capable of illuminating the sample and capturing digital images using various optical systems including those outside the range of autofluorescence such as brightfield imaging. In still another embodiment the automated system may include a computer-readable medium that may includes instructions for the automated technique for the analysis of autofluorescence While only certain features of the invention have been illustrated and described herein, many modifications and changes will occur to those skilled in the art. It is, therefore, to be understood that the appended claims are intended to cover all such modifications and changes as fall within the true spirit of the invention.

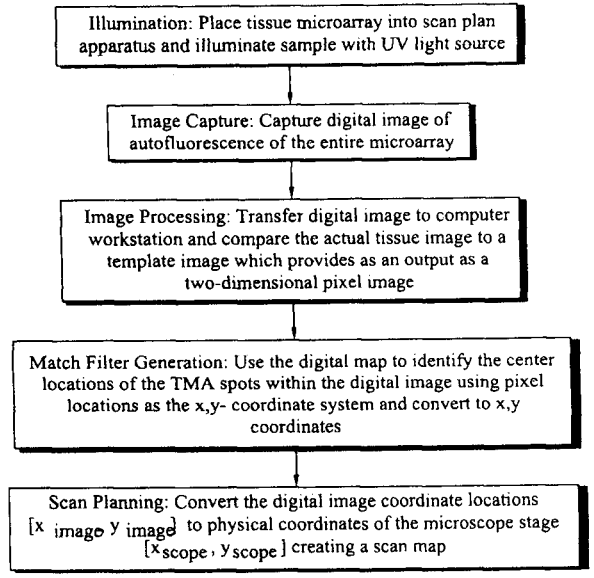

The invention claimed is:

1. A method for locating a substantially circular-shaped tissue sample positioned on a solid support comprising:
   transmitting light of a preselected wavelength onto a tissue sample, wherein the light induces the tissue sample to autofluoresce;
   identifying center location of the tissue sample using the autofluoresced light;
   correlating coordinates of the center location of the tissue sample on the solid support using a two-dimensional coordinate system wherein the correlating step comprises scoring pixel values of the autofluoresced light from the tissue sample; and
   mapping the coordinates of the tissue sample on the solid support to differentiate tissue sample containing regions from blank regions on the solid support.

2. A method according to claim 1 wherein the identifying step comprises capturing the autofluoresced light from the tissue sample to create a digital image of the tissue sample.

3. A method according to claim 1 wherein the scoring of pixel values comprises converting the spatial pixel information of the digital image of the tissue sample to a spectral domain image.

4. A method according to claim 3 wherein the spectral domain image is generated using a fast Fourier transform of the digital image of the tissue sample.

5. A method according to claim 1 wherein the correlating step further comprising comparing the digital image of the tissue sample with a template image of the solid support.

6. A method according to claim 5 wherein the template image of the solid support is a spectral domain image.

7. A method according to claim 6 wherein the spectral domain image of the solid support is generated using fast Fourier transform of a spatial image of the array.

8. A method according to claim 5 wherein the correlating step comprises:
converting spatial pixel information of the digital image of the tissue sample to a spectral domain image;
converting the spatial pixel information of the digital image of the solid support into a spectral domain image of the solid support; and
creating a composite spectral domain image using a multiplication factor of the spectral domain image of the tissue sample and the spectral domain image of the solid support.

9. A method according to claim 8 wherein the multiplication factor comprises a zero-mean cross-correlation, a normalized power spectral density (PSD) cross-correlation, or a combination thereof.

10. A method according to claim 8 further comprising transforming the composite spectral domain image into a spatial domain image.

11. A method according to claim 10 further comprising transforming the spatial domain image into a two-dimensional coordinate system defined by horizontal and vertical axes.

12. A method according to claim 1 wherein the tissue sample is mounted on a tissue micro-array.

13. A method according to claim 12 wherein the tissue micro-array contains more than one tissue sample.

14. A method according to claim 1 wherein the entire solid support is scanned.

15. A method according to claim 1 wherein the preselected wavelength is 365 nm.

16. A method according to claim 1 further comprising applying a fluorescent label to the tissue sample and scanning the tissue sample using the coordinates of the tissue sample obtained in the mapping step.

17. An apparatus for locating a substantially circular-shaped tissue sample positioned on a solid support comprising:
an imaging microscope having at least one objective lens to acquire images at different magnifications and a stage to hold a tissue sample;
an excitation source to illuminate the tissue sample on the stage;
a digital image device connected to the microscope to acquire and digitize the images of the tissue sample;
a storage device in communication with the digital image device capable of storing the digitized images of the tissue sample; and
a processor in communication with the storage device wherein the processor is configured to receive and categorize, the digitized images of the tissue sample and generate one or more match filters based on a correlation factor, and wherein said correlation factor comprises scoring pixel values of the autofluoresced light from the tissue sample.

18. An apparatus according to claim 17 further comprising at least one of a display device for displaying one or more of the images and a transmitting device for transmitting digital information to a remote location.

19. An apparatus according to claim 17 further comprising a controller and a machine-readable medium comprising instructions which when executed by the controller causes an apparatus to locate a substantially circular-shaped tissue sample positioned on a solid support.

20. An apparatus according to claim 17 wherein the apparatus is incorporated as components of an analytical device.

21. The apparatus of claim 20 wherein the analytical device is capable of staining and imaging tissue micro-arrays.

* * * * *

UNITED STATES PATENT AND TRADEMARK OFFICE
CERTIFICATE OF CORRECTION

PATENT NO.        : 8,063,385 B2
APPLICATION NO.   : 12/474306
DATED             : November 22, 2011
INVENTOR(S)       : Filkins et al.

It is certified that error appears in the above-identified patent and that said Letters Patent is hereby corrected as shown below:

The title page showing the illustrative figure should be deleted to be replaced with the attached title page.

In the drawing sheet, consisting of Fig. 1, should be deleted to be replaced with the drawing sheet, consisting of Fig. 1, as shown on the attached page.

In Column 4, Line 18, delete "autofluorescene" and insert -- autofluorescence --, therefor.

Signed and Sealed this
Twelfth Day of June, 2012

David J. Kappos
*Director of the United States Patent and Trademark Office*

(12) United States Patent
Filkins et al.

(10) Patent No.: US 8,063,385 B2
(45) Date of Patent: Nov. 22, 2011

(54) METHOD AND APPARATUS FOR ULTRAVIOLET SCAN PLANNING

(75) Inventors: Robert John Filkins, Niskayuna, NY (US); Robert William Tait, Niskayuna, NY (US); Kevin Bernard Kenny, Niskayuna, NY (US); Christina Chirappuram Royce, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 349 days.

(21) Appl. No.: 12/474,306

(22) Filed: May 29, 2009

(65) Prior Publication Data
US 2010/0301230 A1 Dec. 2, 2010

(51) Int. Cl.
*G01N 21/64* (2006.01)
(52) U.S. Cl. .................. 250/458.1; 250/459.1
(58) Field of Classification Search ............ 250/458.1, 250/459.1
See application file for complete search history.

(56) References Cited

U.S. PATENT DOCUMENTS

| | | |
|---|---|---|
| 6,405,074 B1 | 6/2002 | Banerjee |
| 6,553,135 B1 | 4/2003 | Douglass et al. |
| 6,763,262 B2 | 7/2004 | Hohla et al. |
| 6,775,402 B2 | 8/2004 | Bacus et al. |
| 6,992,760 B2 * | 1/2006 | Mohun et al. ............ 356/317 |
| 7,235,045 B2 | 6/2007 | Wang et al. |
| 7,248,403 B2 | 7/2007 | Nakagawa |
| 2003/0147552 A1 | 8/2003 | Foran et al. |

FOREIGN PATENT DOCUMENTS

| | | |
|---|---|---|
| WO | WO0248692 A1 | 6/2002 |
| WO | WO2005036451 A1 | 4/2005 |
| WO | WO2006134444 A1 | 12/2006 |
| WO | WO2007138369 A1 | 12/2007 |
| WO | WO2009006696 A1 | 1/2009 |

OTHER PUBLICATIONS

PCT International Search Report dated Sep. 24, 2010 and Written Opinion.
Borovansky, "Autofluorescence of Melanins Induced by Ultraviolet Radiation and Near Ultraviolet Light. A Histochemical and Biochemical Study", The Histochemical Journal 2001, 33(5): 273-81.

* cited by examiner

*Primary Examiner* — Mark R Gaworecki
(74) *Attorney, Agent, or Firm* — Eileen W. Gallagher

(57) ABSTRACT

The invention provides method for locating one or more substantially circular-shaped tissue sample positioned on a solid support. The method involves the steps of transmitting light of a preselected wavelength onto a tissue sample, wherein the light induces the tissue sample to autofluoresce, identifying the center location of the tissue sample using the autofluoresced light, correlating the coordinates of the center location of the tissue sample on the solid support using an x, y-coordinate system, and mapping the coordinates of the tissue sample on the solid support to differentiate tissue sample containing regions from blank regions on the solid support. In a second aspect, the invention provides an apparatus for locating one or more substantially circular-shaped tissue sample positioned on a solid support.

21 Claims, 2 Drawing Sheets